United States Patent
Saito et al.

(10) Patent No.: US 9,498,119 B2
(45) Date of Patent: Nov. 22, 2016

(54) ADAPTIVE OPTICS SYSTEM AND CONTROL METHOD OF THE SAME, TESTING APPARATUS AND CONTROL METHOD OF THE SAME, INFORMATION PROCESSING APPARATUS AND CONTROL METHOD OF THE SAME, AND COMPUTER-READABLE STORAGE MEDIUM

(71) Applicant: CANON KABUSHIKI KAISHA, Tokyo (JP)

(72) Inventors: Kenichi Saito, Pittsford, NY (US); Kohei Takeno, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 3 days.

(21) Appl. No.: 14/532,163

(22) Filed: Nov. 4, 2014

(65) Prior Publication Data
US 2015/0131052 A1 May 14, 2015

(30) Foreign Application Priority Data
Nov. 14, 2013 (JP) ................. 2013-236263

(51) Int. Cl.
  A61B 3/14 (2006.01)
  A61B 3/00 (2006.01)
  A61B 3/10 (2006.01)
  A61B 3/12 (2006.01)
(52) U.S. Cl.
  CPC .......... *A61B 3/1015* (2013.01); *A61B 3/0008* (2013.01); *A61B 3/12* (2013.01); *A61B 3/14* (2013.01)

(58) Field of Classification Search
  USPC ................................. 351/206, 246
  See application file for complete search history.

(56) References Cited

U.S. PATENT DOCUMENTS

| | | | |
|---|---|---|---|
| 6,890,076 B2 | 5/2005 | Roorda |
| 7,367,672 B2 | 5/2008 | Akita |
| 8,506,082 B2 | 8/2013 | Saito |
| 8,699,015 B2 | 4/2014 | Saito et al. |
| 2003/0053026 A1 | 3/2003 | Roorda |
| 2007/0010313 A1 | 1/2007 | Akita |
| 2011/0242487 A1 | 10/2011 | Yuasa et al. |
| 2012/0274904 A1 | 11/2012 | Saito et al. |
| 2013/0021576 A1 | 1/2013 | Saito |
| 2014/0055748 A1 | 2/2014 | Saito |
| 2014/0160435 A1 | 6/2014 | Saito |

FOREIGN PATENT DOCUMENTS

| | | |
|---|---|---|
| JP | 2005-501587 A | 1/2005 |
| JP | 2007-014569 A | 1/2007 |
| WO | 03/020121 A1 | 3/2003 |

*Primary Examiner* — Jack Dinh
(74) *Attorney, Agent, or Firm* — Fitzpatrick, Cella, Harper & Scinto

(57) ABSTRACT

An adaptive optics system includes an irradiation unit adapted to irradiate an object with measurement light via a spatial light modulator; a detection unit adapted to detect a wavefront of return light from the object by a microlens array in which a plurality of microlenses are arranged; an acquisition unit adapted to acquire, based on the wavefront detected by the detection unit, correction data for correcting the wavefront by phase wrapping in the spatial light modulator; and a control unit adapted to perform control such that a wavefront discontinuous part formed by the phase wrapping determined by the correction data is held at not less than a predetermined distance from a center of each of the microlenses in the microlens array.

24 Claims, 6 Drawing Sheets

F I G. 1
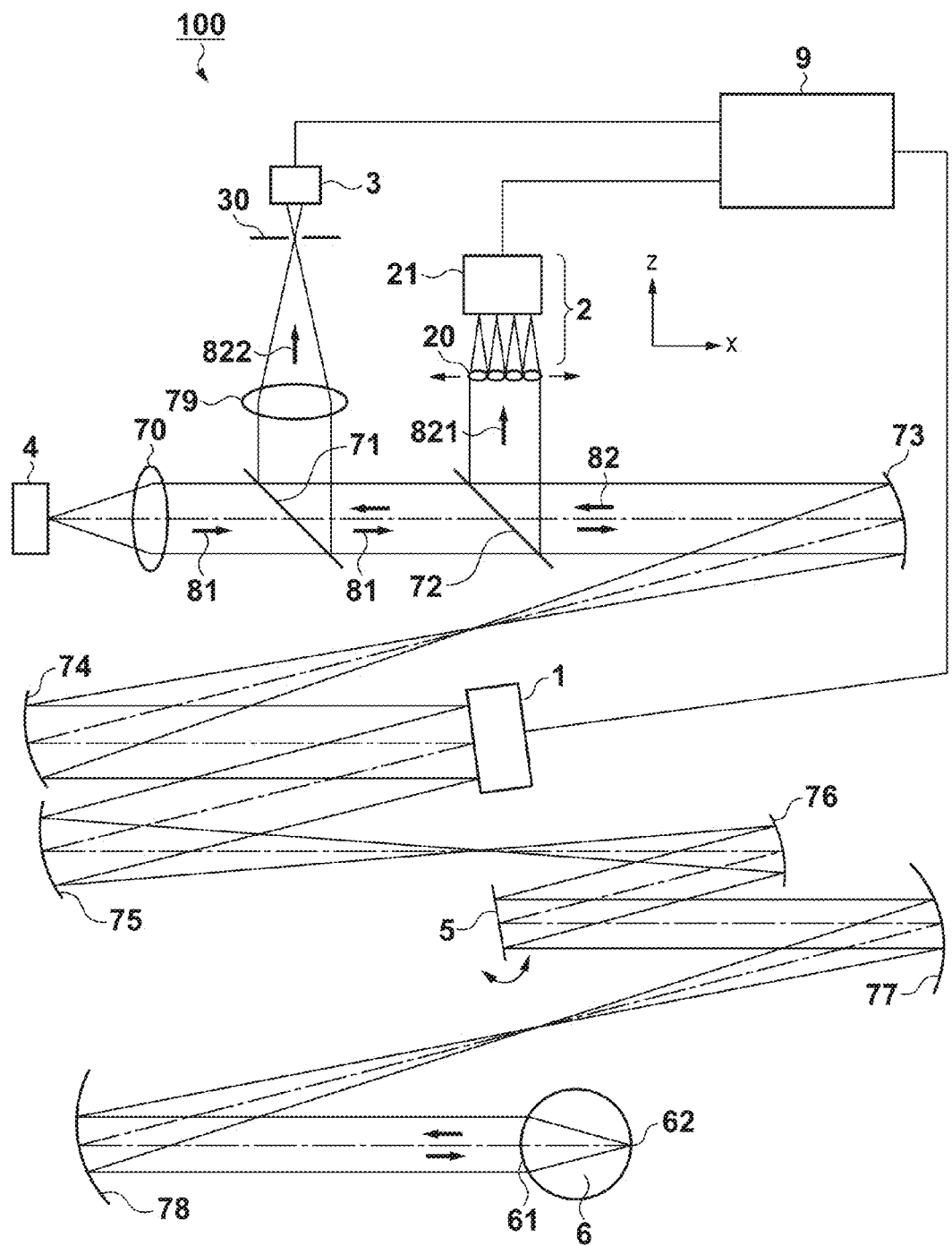

WAVEFRONT CORRECTION DATA
(TWO-DIMENSIONAL)

WAVEFRONT CORRECTION DATA (SECTION)

HS IMAGE

HS IMAGE (ENLARGED VIEW)

ADAPTIVE OPTICS SYSTEM AND CONTROL METHOD OF THE SAME, TESTING APPARATUS AND CONTROL METHOD OF THE SAME, INFORMATION PROCESSING APPARATUS AND CONTROL METHOD OF THE SAME, AND COMPUTER-READABLE STORAGE MEDIUM

BACKGROUND OF THE INVENTION

Field of the Invention

The present invention relates to an adaptive optics system and a control method of the same, a testing apparatus and a control method of the same, an information processing apparatus and a control method of the same, and a computer-readable storage medium and, more particularly, to an adaptive optics system for correcting a wavefront aberration which occurs in an object.

Description of the Related Art

Recently, an adaptive optics (to be referred to as "AO" hereinafter) technique which corrects up to high-order wavefront aberrations by using an active optical element has been put into practical use, and are applied to various fields. In this technique, the wavefront aberration of return light from an object, which is caused by, for example, the optical characteristics of the object itself or variations in measurement environment when the object is irradiated with illumination light, is successively measured by a wavefront sensor and corrected by a wavefront corrector. Examples of the wavefront corrector are a deformable mirror (to be referred to as a "DM" hereinafter), and a spatial light modulator (to be referred to as an "SLM" hereinafter). The AO was initially invented for the purpose of correcting the disturbance of the wavefront caused by the atmospheric fluctuation during astronomical observation, thereby improving the resolution. Recently, however, a testing system for the retina of an eye is particularly attracting attention as an application field having a large effect of introduction.

Known examples of the testing system to be used as an ophthalmologic instrument are a fundus camera, a scanning laser ophthalmoscope which acquires the retina as a two-dimensional image as a plane, and an optical coherence tomography which noninvasively acquires a tomographic image of the retina. In the following description, the scanning laser ophthalmoscope will be referred to as an "SLO", and the optical coherence tomography will be referred to as an "OCT". In the SLO and OCT, a deflector one-dimensionally or two-dimensionally scans irradiation with a light beam on the retina, and synchronously measures reflected light and backscattering light from the retina, thereby acquiring a two-dimensional image or three-dimensional image of the retina.

The spatial resolution (to be referred to as a "lateral resolution" hereinafter) of the acquired image in the plane direction (lateral direction) of the retina is basically determined by the diameter of a beam spot scanned on the retina: the smaller the beam spot diameter, the higher the lateral resolution of the acquired image. To decrease the beam spot diameter condensed on the retina, the diameter of a beam entering the eye need only be increased. However, the surface shape or refractive index of the cornea or crystal lens mainly having a refracting action in the eyeball is not even, and this characteristic of the eye optical system generates a high-order aberration on the wavefront of transmitted light. Even when a thick beam enters, therefore, a spot on the retina cannot condense to a desired diameter but widens. As a consequence, the lateral resolution of the obtained image decreases, and the S/N of the acquired image signal also decreases in a confocal optical system. Accordingly, a general conventional approach is to apply a thin beam of about 1 mm which is hardly influenced by the aberration of the eye optical system, and form a spot of about 20 μm on the retina.

The AO technique is beginning to be introduced as a method for avoiding the influence of the aberration of the eye optical system as described above. The following example has been reported so far. That is, even when a thick beam of about 7.5 mm is applied to the eyeball by using this technique, the beam can be condensed to less than 2 μm close to the diffraction limit on the retina by wavefront compensation, and a high-resolution SLO or OCT image is acquired.

Japanese Patent Laid-Open No. 2005-501587 describes an SLO arrangement in which two-dimensional scanning is performed by condensing a light beam from an illumination light source to the retina, and a wavefront detector detects the wavefront by using a portion of return light reflected from the retina. In this arrangement, a wavefront corrector corrects the wavefronts of illumination light and return light, and an image is formed by using the remaining portion of the return light. It is assumed that the DM is used as the wavefront corrector.

Japanese Patent Laid-Open No. 2007-14569 describes an SLO arrangement based on the assumption that a liquid crystal SLM is used as the wavefront corrector. Unlike the example disclosed in Japanese Patent Laid-Open No. 2005-501587 using the DM, illumination light for image acquisition and wavefront detection illuminates the retina without intervening the SLM.

Generally, when a vapor deposition film is optimized, the DM has characteristics independent of the wavelength over a broad wavelength band and hence can be used in a plurality of applications. However, the DM has drawbacks that calculations are complicated, for example, the setting of a pseudo-inverse matrix necessary to calculate a correction value is complicated, and the cost is very high. On the other hand, the liquid crystal SLM has drawbacks that it has the wavelength dispersion characteristic of a liquid crystal material and the dependence of the diffraction efficiency on the wavelength, and can correct only a polarized component in a specific direction. However, the liquid crystal SLM has advantages that it is more inexpensive than the DM, and control is easy because the measured wavefront aberration shape need only be displayed directly.

As for the drawbacks of the liquid crystal SLM, for example, as for the dependence on polarization, the loss of efficiency can be suppressed to some extent by performing control such that the polarization of the illumination light becomes linear polarization parallel to the modulating operation direction of the SLM. As for the dependence on the wavelength, no problem arises when using a light source having a small wavelength width.

A case in which the liquid crystal SLM is used as the wavefront corrector of the AO system as disclosed in Japanese Patent Laid-Open No. 2007-14569 and a Hartmann Shack wavefront sensor combining a microlens array and two-dimensional imaging element is used as the wavefront detector will be described below. In the following description, the microlens array will be referred to as an "MLA", and the Hartmann Shack wavefront sensor will be referred to as an "HS wavefront sensor". The wavefront corrector and wavefront detector are generally arranged to be optically conjugated. This is so because wavefront shape data detected by the wavefront detector need only be formed as correction data on the wavefront corrector without being processed. This raises the feedback time response of wavefront correction, and also improves the convergence properties. Accordingly, a modulation pattern displayed on the liquid crystal SLM is projected (imaged) on the MLA of the HS wavefront sensor.

In this state, a maximum phase modulation amount of the liquid crystal SLM is only a little more than $2\pi$, that is, only a little more than one wavelength as an optical path length. To correct an aberration amount of a few wavelengths or more, therefore, a correction control signal value is folded for every phase of $2\pi$ (equivalent to one wavelength as an optical path length). Modulation must be performed by thus performing phase wrapping (to be referred to as "PW" hereinafter). Accordingly, a boundary line on which a control signal becomes discontinuous due to PW appears for every phase modulation amount of $2\pi$.

Also, in the HS wavefront sensor, a displacement from a reference position is measured for each spot (a Hartmann Shack image: to be referred to as an "HS image" hereinafter) formed by each micro lens (to be referred to as an "ML" hereinafter) of the MLA. Then, the slope of a wavefront piece between the MLs is calculated from this displacement, and the whole wavefront shape is derived. In this case, if the PW boundary line is projected near the center of each ML, the image formation spot breaks. If the spot shape thus breaks, the spot detection positional accuracy decreases, and this makes it impossible to obtain a correct wavefront.

SUMMARY OF THE INVENTION

The present invention provides a technique of preventing the disturbance of an HS image spot, which occurs due to the positional relationship between a PW pattern of correction data and an MLA, and maintaining the accuracy of wavefront detection, even when using a liquid crystal SLM and HS wavefront sensor.

According to one aspect of the present invention, an adaptive optics system includes: an irradiation unit adapted to irradiate an object with measurement light via a spatial light modulator; a detection unit adapted to detect a wavefront of return light from the object by a microlens array in which a plurality of microlenses are arranged; an acquisition unit adapted to acquire, based on the wavefront detected by the detection unit, correction data for correcting the wavefront by phase wrapping in the spatial light modulator; and a control unit adapted to perform control such that a wavefront discontinuous part formed by the phase wrapping determined by the correction data is held at not less than a predetermined distance from a center of each of the microlenses in the microlens array.

According to another aspect of the present invention, a testing apparatus for irradiating an object with measurement light and acquiring an image of the object by return light, includes: a spatial light modulator adapted to modulate the measurement light by phase wrapping; a detection unit adapted to detect a wavefront of the return light from the object by a microlens array in which a plurality of microlenses are arranged; and a control unit adapted to perform control such that a wavefront discontinuous part formed by the phase wrapping is held at not less than a predetermined distance from a center of each of the microlenses in the microlens array.

According to still another aspect of the present invention, an information processing apparatus for controlling an operation of an adaptive optics system including an irradiation unit adapted to irradiate an object with measurement light via a spatial light modulator, and a detection unit adapted to detect a wavefront of return light from the object by a microlens array in which a plurality of microlenses are arranged, includes: an acquisition unit adapted to acquire, based on the wavefront detected by the detection unit, correction data for correcting the wavefront by phase wrapping in the spatial light modulator; and a control unit adapted to perform control such that a wavefront discontinuous part formed by the phase wrapping determined by the correction data is held at not less than a predetermined distance from a center of each of the microlenses in the microlens array.

According to yet another aspect of the present invention, a control method of an adaptive optics system, includes: an irradiation step of causing an irradiation unit to irradiate an object with measurement light via a spatial light modulator; a detection step of causing a detection unit to detect a wavefront of return light from the object by a microlens array in which a plurality of microlenses are arranged; an acquisition step of causing an acquisition unit to acquire, based on the wavefront detected in the detection step, correction data for correcting the wavefront by phase wrapping in the spatial light modulator; and a control step of causing a control unit to perform control such that a wavefront discontinuous part formed by the phase wrapping determined by the correction data is held at not less than a predetermined distance from a center of each of the microlenses in the microlens array.

According to still yet another aspect of the present invention, a control method of a testing apparatus for irradiating an object with measurement light and acquiring an image of the object by return light, includes: a step of causing a spatial light modulator to modulate the measurement light by phase wrapping; a detection step of causing a detection unit to detect a wavefront of the return light from the object by a microlens array in which a plurality of microlenses are arranged; and a control step of causing a control unit to perform control such that a wavefront discontinuous part formed by the phase wrapping is held at not less than a predetermined distance from a center of each of the microlenses in the microlens array.

According to yet still another aspect of the present invention, a control method of an information processing apparatus for controlling an operation of an adaptive optics system including an irradiation unit adapted to irradiate an object with measurement light via a spatial light modulator, and a detection unit adapted to detect a wavefront of return light from the object by a microlens array in which a plurality of microlenses are arranged, includes: an acquisition step of causing an acquisition unit to acquire, based on the wavefront detected by the detection unit, correction data for correcting the wavefront by phase wrapping in the spatial light modulator; and a control step of causing a control unit to perform control such that a wavefront discontinuous part formed by the phase wrapping determined by the correction data is held at not less than a predetermined distance from a center of each of the microlenses in the microlens array.

Further features of the present invention will become apparent from the following description of exemplary embodiments (with reference to the attached drawings).

BRIEF DESCRIPTION OF THE DRAWINGS

FIG. 1 is a view showing the arrangement of a scanning laser ophthalmoscope using an adaptive optics system;

DESCRIPTION OF THE EMBODIMENTS

Figure 2:
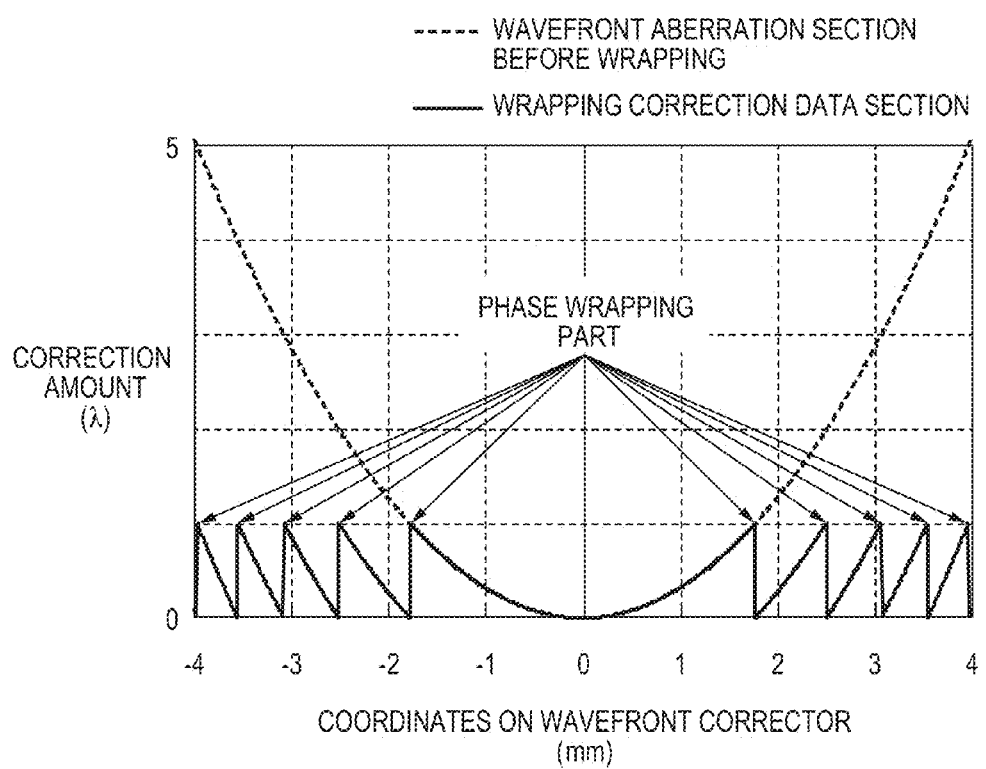
FIG. 2 is a conceptual view of phase wrapping.

Embodiments of the present invention will be explained in detail below with reference to the accompanying drawings.

(Arrangement of AO-SLO)

FIG. 1 is a view schematically showing the arrangement of a scanning laser ophthalmoscope (to be referred to as an "AO-SLO" hereinafter) 100 using an adaptive optical (AO) system, as an image acquisition apparatus (testing apparatus) according to the first embodiment of the present invention. An illumination light source 4 for image acquisition generates low-coherence light having a central wavelength of 840 nm and a wavelength width of 20 nm, and emits the low-coherence light as diverging light. This diverging light emitted from the light source 4 is collimated by a collimator lens 70, and transmitted as illumination light 81 through beam splitters 71 and 72. After that, the illumination light 81 enters a liquid crystal SLM (Spatial Light Modulator) 1 via concave mirrors 73 and 74.

Light reflected by the SLM 1 enters a reflective deflector 5 via concave mirrors 75 and 76, and is reflectively deflected by the reflective deflector 5. The reflectively deflected light enters an eye 6 to be examined as an object via concave mirrors 77 and 78, and is condensed and scanned on a retina 62. In this embodiment, the diameter of the light entering the eye 6 to be examined is about 6 mm. Thus, the measurement light irradiates the object via the spatial light modulator.

Return light 82 diffused and reflected on the retina 62 is given aberration by an anterior eye part 61 of the eye to be examined, and propagates through an optical path reverse to that described above. After that, a portion 821 of the return light 82 is reflected by the beam splitter 72, and enters an HS (Hartmann Shack) sensor 2. The HS sensor 2 forms a plurality of spots (HS images) on an imaging element 21 by an MLA (Micro Lens Array) 20 in which a large number of MLs (Micro Lenses) are periodically arranged. That is, the HS sensor 2 detects the wavefront of the return light from the object by the micro lens array formed by arranging the plurality of microlenses. The HS sensor 2 transmits image data of HS images of the detected wavefront to a personal computer (information processing apparatus) 9.

The personal computer 9 calculates the slope of a wavefront normal from a displacement amount from a reference position for each spot in an effective region (equivalent to the pupil or incident beam diameter) to be used to calculate the wavefront, calculates a wavefront aberration in the effective region of the detected return light 82, and forms wavefront correction data. That is, based on the wavefront detected by the HS sensor 2, correction data for correcting the wavefront by phase wrapping in the SLM 1 is acquired. This wavefront correction data is transmitted to the SLM 1 to drive it. Consequently, the illumination light 81 corrected and reflected by the SLM 1 and entering the eye 6 to be examined is given aberration which cancels the aberration of the eye 6 to be examined. As a result, a spot to be condensed to the retina 62 after being transmitted through the anterior eye part is well condensed with a less aberration. Note that the personal computer 9 controls its operation in accordance with a predetermined computer program.

The return light 82 from the eye 6 to be examined is also corrected by the SLM 1 to have a less aberration, and the wavefront aberration measurement value obtained by the HS sensor 2 decreases. At the same time, the other light 822 of the return light 82 transmitted through the beam splitter 72 is reflected by the beam splitter 71, and condensed on a pinhole 30 by a lens 79. A component having passed through the pinhole 30 is detected by a photodetector 3, and converted into an electrical signal. The electrical signal is transmitted to the personal computer 9, and forms an image in synchronism with the reflective deflection timing of the reflective deflector 5. By repeating this feedback, the wavefront aberration is further minimized, and the spots on the retina 62 and pinhole 30 decrease to the diffraction limiting level. This makes it possible to acquire an image having a high brightness, high contrast, and high resolution. When the diffraction-limit aberration can be achieved, a high resolution of about 3 μm can be realized.

The optical system is so designed that the HS sensor 2, the SLM 1, the reflective deflector 5, and the anterior eye part 61 of the eye to be examined are optically conjugated. The retina 62 and pinhole 30 also have an image formation relationship. Furthermore, when light having a wavelength different from that of the illumination light source for image acquisition is used as the illumination light for wavefront detection, a dichroic mirror is used instead of a beam splitter as the element 72 for branching the optical path to the HS sensor 2. This is so because the dichroic mirror transmits the wavelength of the image acquisition illumination light, and reflects the wavelength of the wavefront detection illumination light.

(Decrease in Wavefront Detection Accuracy Caused by Boundary Line of Phase Wrapping)

A maximum phase modulation amount of a liquid crystal SLM is only a little more than $2\pi$, that is, only a little more than one wavelength as an optical path length. To correct an aberration amount of a few wavelengths or more, therefore, modulation is performed by PW (Phase Wrapping) which performs folding for every phase of $2\pi$ (equivalent to one wavelength as an optical path length). As shown in a correction data sectional view of FIG. 2, a discontinuous part formed by PW appears for every phase modulation amount λ. This discontinuous part will be called a phase wrapping part (to be referred to as a "PW part").

Figure 3A:
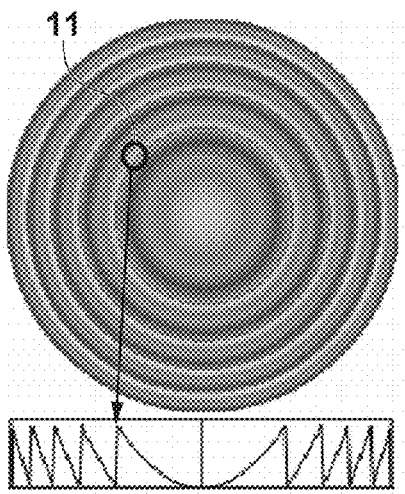
FIGS. 3A, 3B, and 3C are views showing the characteristics of HS image spots formed by phase wrapping of an SLM.
Figure 3B:
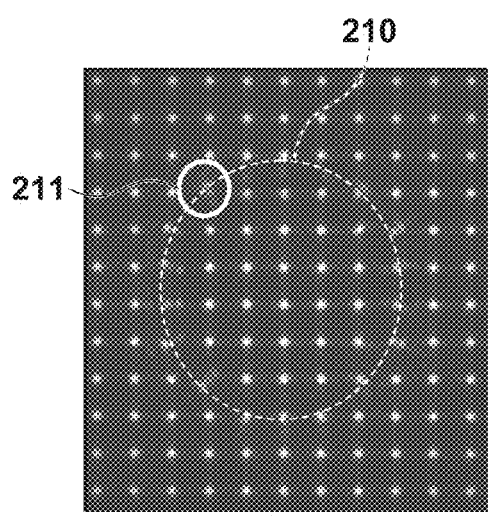
Figure 3C:
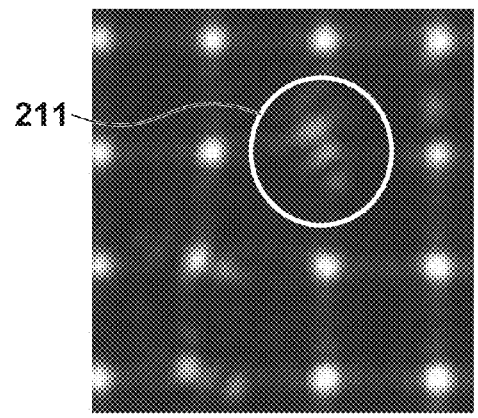

On the other hand, each spot position of the HS image is generally calculated as the barycentric position or intensity peak position of the spot from the image data acquired by the imaging element 21. Assume that when the aberration of a given eye to be examined is measured and wavefront correction is performed, a wavefront discontinuous part formed by PW, which is indicated by a broken line 210 on an HS image shown in each of FIGS. 3B and 3C, is projected near the center of the a given ML of the HS sensor. In this case, a spot of the HS image is disturbed as shown in a portion 211 enclosed with a white circle, so the wavefront aberration cannot correctly be measured. Accordingly, even when the wavefront aberration finally obtained by wavefront correction is regarded as being minimized as the measurement value of the HS sensor 2, the aberration actually remains in the return light 82, so the image quality is not the best quality.

To prevent the above-mentioned problem, the wavefront discontinuous part formed by PW need only enter a position apart from the center of each ML in the effective region to be used calculate at least the wavefront in the HS sensor 2. However, the wavefront naturally changes from one eye to be examined to another, so the above-mentioned problem unavoidably arises at a predetermined ratio. This makes it necessary to grasp the relationship between the coordinate point of the PW part and the coordinate point of each ML in real time, and apply feedback so that the two coordinate points do not match.

(Improvement of Wavefront Detection Accuracy by Shift of MLA)

As a mechanism for preventing the wavefront discontinuous part formed by PW from matching the center of each ML, this embodiment includes a moving mechanism capable of relatively shifting the MLA 20 of the HS sensor 2 in an x-y plane perpendicular to the optical axis, with respect to the entering return light 821.

First, the HS sensor 2 measures the aberration of the eye 6 to be examined while the SLM 1 is not displaying any wavefront correction data, and the SLM 1 displays wavefront correction data corresponding to the aberration. Coordinates $P_i(x_i, y_i)$ of PW parts, such as a black-circle portion 11 on wavefront corrector data shown in FIG. 3A, which are generated in this state are calculated. In this embodiment, i is an integer from 1 to m, and m is the number of data points corresponding to the PW parts.

The SLM 1 and MLA 20 are arranged to be optically conjugated. Letting $\beta$ be the lateral magnification between the SLM 1 and MLA 20, therefore, an image $P_i'$ of $P_i$ formed on the MLA 20 is $P_i'(-\beta \cdot x_i, -\beta \cdot y_i)$.

Letting $Q_j(x_j, y_j)$ (j=1 to n; n is the total number of MLs in the effective region to be used in wavefront detection) be the coordinate point of the center of each ML, when a smallest distance $\min|P_i'Q_j|$ of distances $|P_i'Q_j|$ between $P_i$ and $Q_j$ satisfies:

$$\min|P_i'Q_j| < d_0 \quad (1)$$

with respect to a specific value $d_0$ ($0 < d_0 < p/4$), the above-mentioned shift mechanism shifts the MLA 20 by $d_0$ in a $P_i'Q_j$ direction. p is the MLA pitch. Since the MLA 20 is thus shifted, wavefront calculations must be performed by shifting a segment region on the imaging element with respect to each ML.

Figure 4:
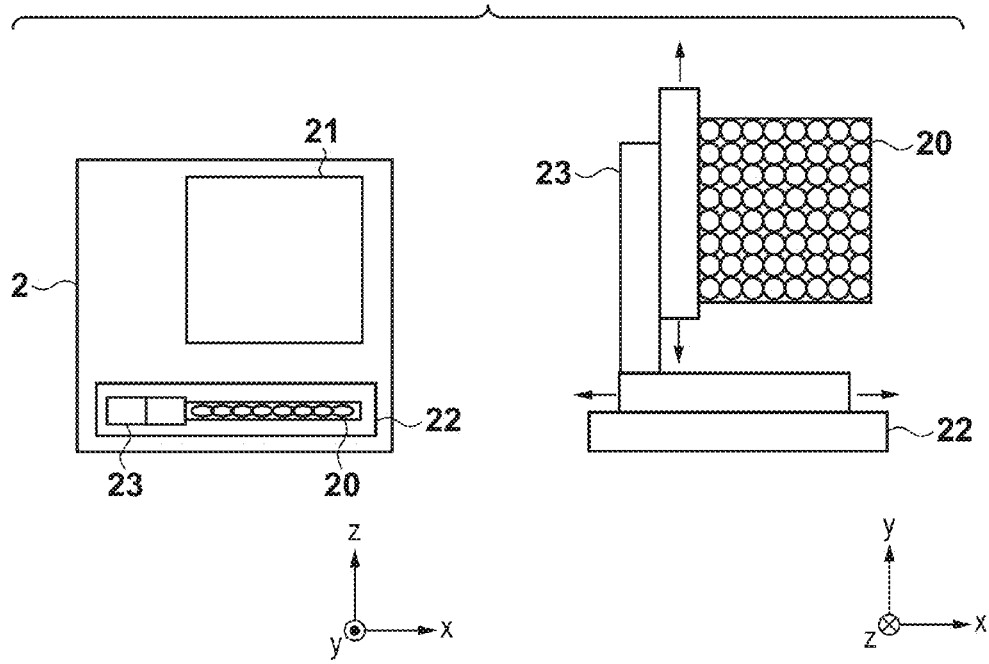
FIG. 4 is a conceptual view of a microlens array moving mechanism.

FIG. 4 shows the shift mechanism of the MLA 20. The upper view is a plan view (the z-x plane), and the lower view is a front view (the x-y plane). The HS sensor 2 includes the MLA 20, the imaging element 21, an x stage 22, and a y stage 23. When the PW position of the correction data satisfies above-mentioned condition (1), the x and y stages move by predetermined amounts so as to shift the MLA 20 by $d_0$ in the $P_i'Q_j$ direction.

Figure 5:
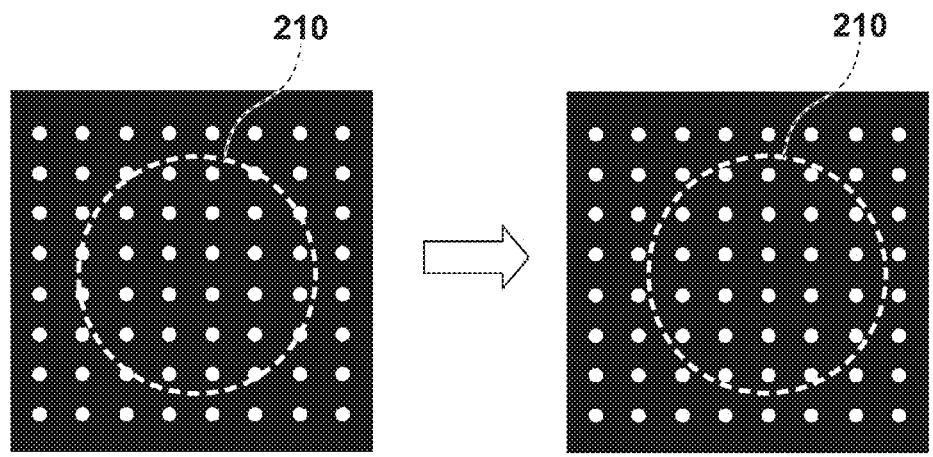
FIG. 5 is a conceptual view when a phase wrapping part is moved on an HS sensor.

Consequently, as shown in FIG. 5, the position of the PW part represented by the broken line 210 on the MLA can be shifted so as not to overlap the central position of each ML (so as not to form any point meeting (1)). When there is no point meeting (1), the MLA 20 is not shifted. By thus performing control such that the minimum value of the distance between the wavefront discontinuous part to be projected onto the MLA 20 and the central position of each ML exceeds a predetermined value, it is possible to hold a predetermined distance or more between the wavefront discontinuous part and each ML, and prevent the disturbance of the HS spot.

Whether to shift the MLA 20 may also be determined based on the value of the peak intensity of each spot in an actual HS image, instead of condition (1). If the peak intensity of each spot in the HS image is $I_j$ (j=1 to n; n is the total number of MLs in the effective region to be used in wavefront detection) when initial correction data is displayed on the SLM 1, the MLA 20 is shifted by $d_0$ in the x or y direction in accordance with the aberration of the eye 6 to be examined if a spot k which satisfies:

$$I_k < a \cdot \text{Average}[I_1 \sim I_n] (0 < a < 1) \quad (2)$$

exists with respect to Average $[I_1$ to $I_n]$ as the average value of the peak intensities. The value of a coefficient a must be a minimum value having no influence on a calculation error of the barycentric position of the spot. For example, the coefficient a is desirably about 0.7 to 0.8. The quality of an HS image may also be ensured by thus performing control so that the peak intensity of each condensing spot formed on the MLA 20 by the return light modulated in the SLM 1 exceeds a predetermined value.

When shifting the MLA 20 by using condition (1) or (2), Hartmann image spots for given j or k may improve, but a spot may be disturbed for the coordinate point Q of another ML because condition (1) or (2) is met. If this is the case, measurements are performed by changing the shift direction or changing the shift amount several times, and the measurement results are combined. This makes it possible to calculate the wavefront by forming a Hartmann image in which all spots are good.

Furthermore, even when condition (1) or (2) is not met in the determination by the first correction, the condition may be met with the elapse of time because the eye to be examined sometimes moves in the direction perpendicular to the optical axis with time. Accordingly, the determination of (1) or (2) and the shift operation of the MLA 20 are desirably always performed while wavefront detection is performed.

In this embodiment, the relative positions of each ML and the PW part are shifted by shifting the MLA 20, but an object to be moved is not limited to the MLA 20. For example, the whole HS sensor 2 can be mounted on a stage and shifted, and the same effect as above can be obtained by a method of shifting the whole AO-SLO apparatus 100 relative to the eye to be examined in the direction perpendicular to the optical axis.

In this embodiment as described above, control is so performed that the wavefront discontinuous part formed by phase wrapping determined by correction data is held at a predetermined distance or more from the center of each ML in the MLA 20. Therefore, this embodiment can effectively prevent a decrease in wavefront detection accuracy caused when the wavefront discontinuous part enters the center of the ML.

Also, in this embodiment, control is performed such that the wavefront discontinuous part is held at a predetermined distance or more from the center of each ML by changing the relative positional relationship between the SLM 1 and MLA 20 by moving the MLA 20 in the plane of the MLA 20. Accordingly, this embodiment can directly prevent the wavefront discontinuous part from entering a position close to the center of the ML. Note that the example in which the relative positional relationship between the SLM 1 and MLA 20 is changed by moving the MLA 20 has been explained in this embodiment, but the present invention is not limited to this as described previously.

Next, AO-SLO using an adaptive optics system of the second embodiment of the present invention will be explained. In the first embodiment, the positional relationship between the phase wrapping part (PW part) and each ML is optimized by shifting the MLA 20 or HS sensor 2. By contrast, this embodiment achieves an equal effect by a method of processing wavefront correction data to be displayed on an SLM 1, instead of correcting the positional relationship between the wavefront and an MLA by a physical shift. Since the arrangement of the AO-SLO is the same as that of the first embodiment, differences from the first embodiment will mainly be explained in this embodiment.

Figure 6A:
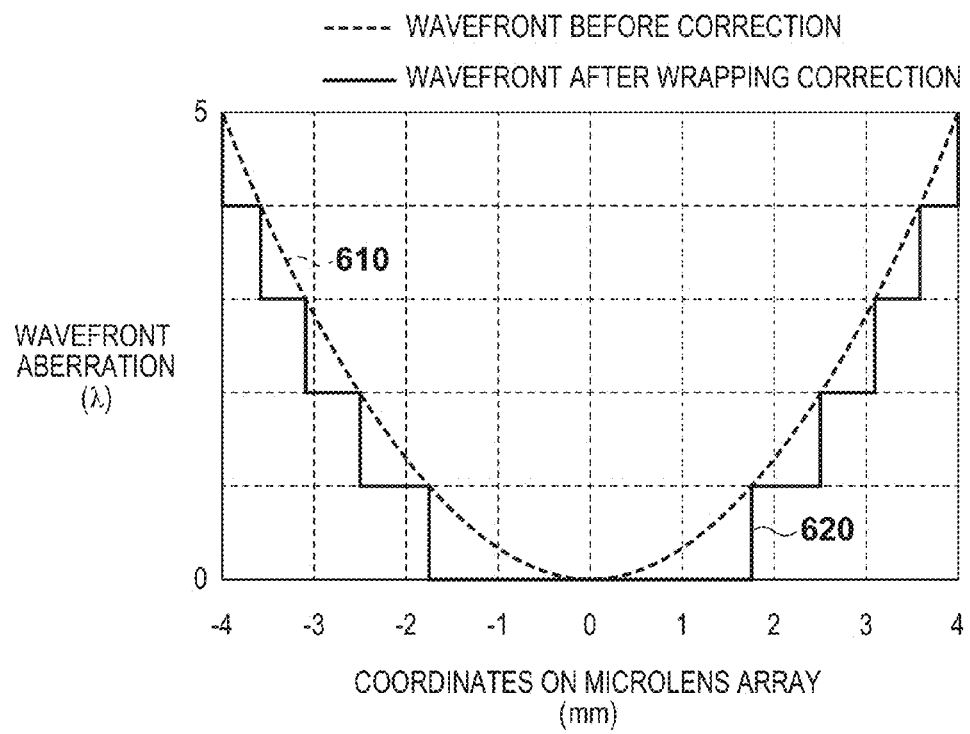
FIGS. 6A and 6B are views for explaining a phase wrapping part obtained by the addition of a piston aberration component.
Figure 6B:
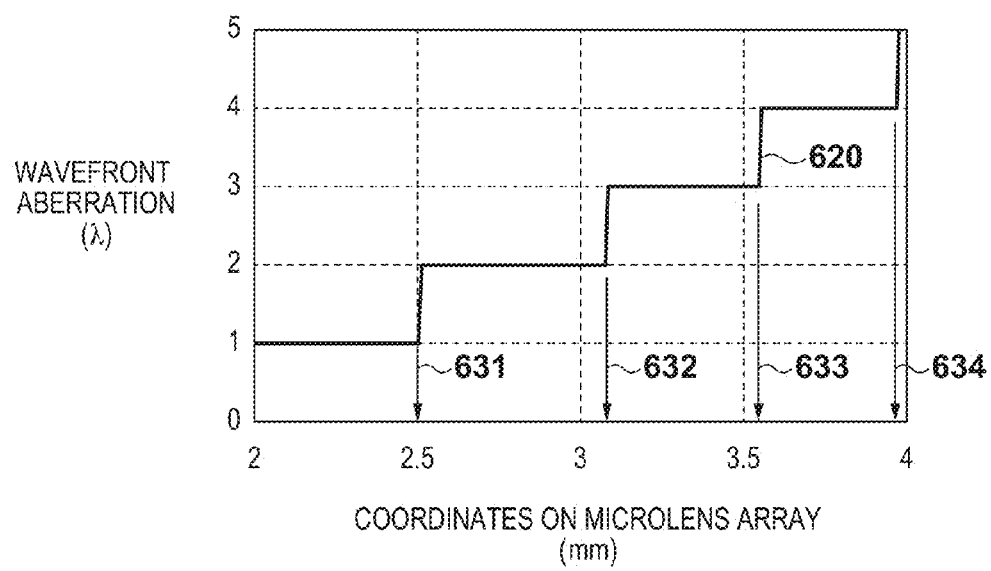

Generally, when the wavefront aberration of return light from an eye to be examined has a shape as indicated by a broken line 610 shown in FIG. 6A, the wavefront of the return light corrected by the SLM 1 has a wavefront state as indicated by a solid line 620 shown in FIGS. 6A and 6B if phase wrapping is performed as shown in FIG. 2. When an aberration amount is an integral multiple of a wavelength λ, this means that the phase difference is 2π, so it is impossible to distinguish between phases. In an ideal case, the wavefront of the solid line 620 is processed as a plane wave. In practice, however, the disturbance of a spot in a Hartmann image increases most when discontinuous parts of the solid line 620 indicated by arrows 631 to 634 in FIG. 6B enter the center of a given ML.

Figure 7A:
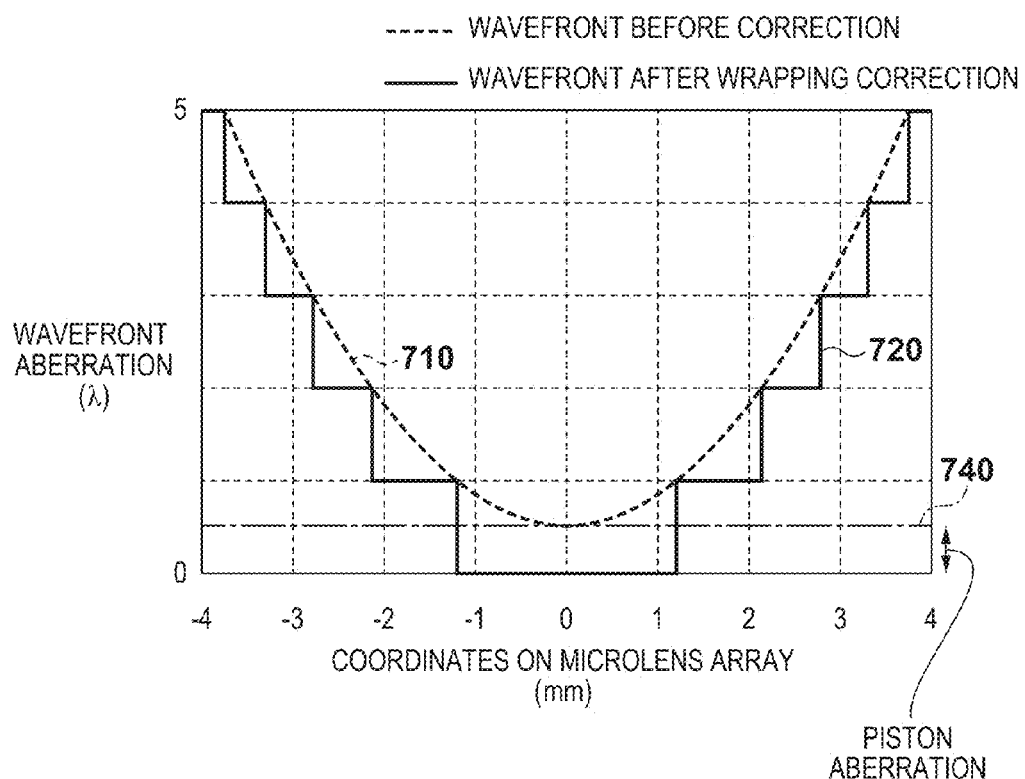
FIGS. 7A and 7B are views for explaining a phase wrapping part obtained by the addition of a piston aberration portion.
Figure 7B:
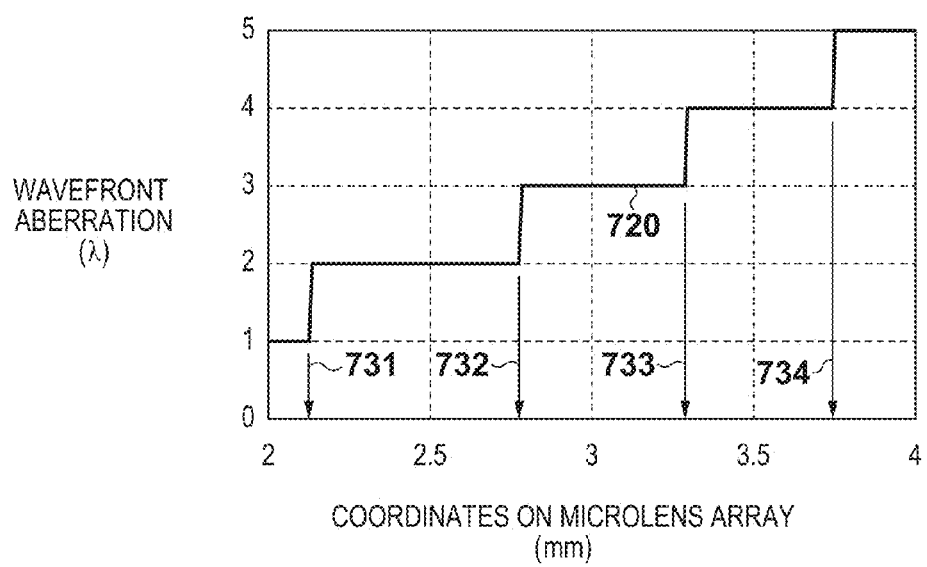

Accordingly, a given amount of a piston aberration component as indicated by an alternate long and short dashed line 740 in FIG. 7A is added to the wavefront correction data to be displayed on the SLM 1. This shifts the wavefront before correction from the broken line 610 in FIG. 6A to a broken line 710 in FIG. 7A, and shifts the wavefront of the return light corrected by the SLM 1 to a solid line 720. As a consequence, the positions of PW parts indicated by arrows 731 to 734 in FIG. 7B shift from those of the initial wavefront correction data indicated by the arrows 631 to 634 in FIG. 6B. In this embodiment, therefore, it is possible to improve the wavefront detection accuracy by avoiding the overlap of the ML center and PW part without mechanically shifting the positional relationship between the MLA and SLM. Letting α be the slope of the wavefront at a coordinate point $Q_k$ of the ML at which min$|P_i'Q_j|$, the aberration amount to be added need only have a value of $\alpha \cdot d_0$ or more.

If there is no point meeting condition (1) or (2), no piston aberration is added to the wavefront correction data. In addition, as in the first embodiment, the determination of condition (1) or (2) and the addition of the piston aberration are desirably always performed while wavefront detection is performed. Note that when the piston aberration is added, the reflected light from the SLM slightly shifts, but the shift amount is very small and absorbed in the process of wavefront correction, so the influence is almost negligible.

In this embodiment as described above, control is so performed that the wavefront discontinuous part is held at a predetermined distance or more from the center of each ML by adding a predetermined aberration component to the correction data. In this embodiment, therefore, it is possible to prevent, without using any special moving mechanism, the wavefront discontinuous part from entering the ML center and decreasing the wavefront detection accuracy.

In each embodiment described above, it is possible to perform accurate wavefront detection regardless of an aberration shape and acquire a good image even in an adaptive optics system using a liquid crystal SLM and HS wavefront sensor.

The present invention can provide a technique of maintaining the accuracy of wavefront detection by preventing the disturbance of a spot in an HS image, which occurs due to the positional relationship between a PW pattern of correction data and an MLA.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-236263, filed on Nov. 14, 2013, which is hereby incorporated by reference herein in its entirety.

What is claimed is:
1. An adaptive optics system comprising:
an irradiation unit adapted to irradiate an object with measurement light via a spatial light modulator;
a detection unit adapted to detect a wavefront of return light from the object by a microlens array in which a plurality of microlenses are arranged;
an acquisition unit adapted to acquire, based on the wavefront detected by said detection unit, correction data for correcting the wavefront by phase wrapping in said spatial light modulator; and
a control unit adapted to perform control such that a wavefront discontinuous part formed by the phase wrapping determined by the correction data is held at not less than a predetermined distance from a center of each of said microlenses in said microlens array.

2. The system according to claim 1, wherein said control unit performs control such that the wavefront discontinuous part is held at not less than the predetermined distance from the center of each of said microlenses, by using a moving unit adapted to change a relative positional relationship between said spatial light modulator and said microlens array.

3. The system according to claim 2, wherein said moving unit changes the relative positional relationship by moving said microlens array in a plane of said array.

4. The system according to claim 3, wherein said control unit performs control such that a minimum value of a distance between the wavefront discontinuous part projected onto said microlens array and a central position of each of said microlenses exceeds a predetermined value.

5. The system according to claim 3, wherein said control unit performs control such that a peak intensity of each condensing spot formed on said microlens array by the return light modulated by said spatial light modulator exceeds a predetermined value.

6. The system according to claim 2, wherein said control unit performs control such that a minimum value of a distance between the wavefront discontinuous part projected onto said microlens array and a central position of each of said microlenses exceeds a predetermined value.

7. The system according to claim 2, wherein said control unit performs control such that a peak intensity of each condensing spot formed on said microlens array by the return light modulated by said spatial light modulator exceeds a predetermined value.

8. The system according to claim 1, wherein said control unit performs control such that the wavefront discontinuous part is held at not less than the predetermined distance from the center of each of said microlenses, by adding a predetermined aberration component to the correction data.

9. The system according to claim 8, wherein said control unit performs control such that a minimum value of a distance between the wavefront discontinuous part projected onto said microlens array and a central position of each of said microlenses exceeds a predetermined value.

10. The system according to claim 1, wherein said control unit performs control such that a minimum value of a distance between the wavefront discontinuous part projected onto said microlens array and a central position of each of said microlenses exceeds a predetermined value.

11. The system according to claim 8, wherein said control unit performs control such that a peak intensity of each condensing spot formed on said microlens array by the return light modulated by said spatial light modulator exceeds a predetermined value.

12. The system according to claim 1, wherein said control unit performs control such that a peak intensity of each condensing spot formed on said microlens array by the return light modulated by said spatial light modulator exceeds a predetermined value.

13. A testing apparatus for irradiating an object with measurement light and acquiring an image of the object by return light, comprising:
- a spatial light modulator adapted to modulate the measurement light by phase wrapping;
- a detection unit adapted to detect a wavefront of the return light from the object by a microlens array in which a plurality of microlenses are arranged; and
- a control unit adapted to perform control such that a wavefront discontinuous part formed by the phase wrapping is held at not less than a predetermined distance from a center of each of said microlenses in said microlens array.

14. An information processing apparatus for controlling an operation of an adaptive optics system including an irradiation unit adapted to irradiate an object with measurement light via a spatial light modulator, and a detection unit adapted to detect a wavefront of return light from the object by a microlens array in which a plurality of microlenses are arranged, comprising:
- an acquisition unit adapted to acquire, based on the wavefront detected by said detection unit, correction data for correcting the wavefront by phase wrapping in said spatial light modulator; and
- a control unit adapted to perform control such that a wavefront discontinuous part formed by the phase wrapping determined by the correction data is held at not less than a predetermined distance from a center of each of said microlenses in said microlens array.

15. A computer-readable storage medium storing a computer program for causing a computer to function as each unit of an information processing apparatus cited in claim 14.

16. A control method of an adaptive optics system, comprising:
- an irradiation step of causing an irradiation unit to irradiate an object with measurement light via a spatial light modulator;
- a detection step of causing a detection unit to detect a wavefront of return light from the object by a microlens array in which a plurality of microlenses are arranged;
- an acquisition step of causing an acquisition unit to acquire, based on the wavefront detected in the detection step, correction data for correcting the wavefront by phase wrapping in the spatial light modulator; and
- a control step of causing a control unit to perform control such that a wavefront discontinuous part formed by the phase wrapping determined by the correction data is held at not less than a predetermined distance from a center of each of the microlenses in the microlens array.

17. A control method of a testing apparatus for irradiating an object with measurement light and acquiring an image of the object by return light, comprising:
- a step of causing a spatial light modulator to modulate the measurement light by phase wrapping;
- a detection step of causing a detection unit to detect a wavefront of the return light from the object by a microlens array in which a plurality of microlenses are arranged; and
- a control step of causing a control unit to perform control such that a wavefront discontinuous part formed by the phase wrapping is held at not less than a predetermined distance from a center of each of the microlenses in the microlens array.

18. A control method of an information processing apparatus for controlling an operation of an adaptive optics system including an irradiation unit adapted to irradiate an object with measurement light via a spatial light modulator, and a detection unit adapted to detect a wavefront of return light from the object by a microlens array in which a plurality of microlenses are arranged, comprising:
- an acquisition step of causing an acquisition unit to acquire, based on the wavefront detected by the detection unit, correction data for correcting the wavefront by phase wrapping in the spatial light modulator; and
- a control step of causing a control unit to perform control such that a wavefront discontinuous part formed by the phase wrapping determined by the correction data is held at not less than a predetermined distance from a center of each of the microlenses in the microlens array.

19. A testing apparatus for irradiating an object with measurement light and acquiring an image of the object by return light, said testing apparatus comprising:

a spatial light modulator adapted to modulate the measurement light by phase wrapping;

a detection unit adapted to detect a wavefront of the return light from the object by a microlens array in which a plurality of microlenses are arranged; and a control unit adapted to change a relative positional relationship between said spatial light modulator and said detection unit in a direction perpendicular to the optical axis of the return light when a wavefront discontinuous part formed by the phase wrapping is positioned at the center of a microlens in said microlens array.

20. The testing apparatus according to claim 19, wherein said control unit changes the positional relationship by controlling a moving unit adapted to move said microlens array in the direction.

21. The testing apparatus according to claim 20, wherein said control unit performs control such that a minimum value of a distance between the wavefront discontinuous part projected onto said microlens array and a central position of the microlens exceeds a predetermined value.

22. A testing apparatus for irradiating an object with measurement light and acquiring an image of the object by return light, said testing apparatus comprising:

a spatial light modulator adapted to modulate the measurement light by phase wrapping;

a detection unit adapted to detect a wavefront of the return light from the object by a microlens array in which a plurality of microlenses are arranged; and a control unit adapted to move the position of the phase wrapping in said spatial light modulator when a wavefront discontinuous part formed by the phase wrapping is positioned at the center of a microlens in said microlens array.

23. The testing apparatus according to claim 22, wherein said control unit is adapted to:

acquire, based on the wavefront detected by said detection unit, correction data for correcting the wavefront by phase wrapping in said spatial light modulator; and move the position of the phase wrapping in said spatial light modulator by adding a predetermined aberration component to the correction data.

24. The testing apparatus according to claim 23, wherein said control unit is adapted to add the predetermined aberration component to the correction data such that a peak intensity of a condensing spot by the microlens exceeds a predetermined value.

* * * * *